(12) United States Patent
Tanner et al.

(10) Patent No.: US 7,008,370 B2
(45) Date of Patent: Mar. 7, 2006

(54) METHOD AND DEVICE FOR TRANSCRANIAL MAGNETIC STIMULATION

(75) Inventors: Phillipp Tanner, München (DE); Andreas Hartlep, München (DE); Henrik Wist, München (DE); Kerstin Wendicke, München (DE); Thomas Weyh, München (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 0 days.

(21) Appl. No.: 10/820,290

(22) Filed: Apr. 8, 2004

(65) Prior Publication Data

US 2004/0193002 A1 Sep. 30, 2004

Related U.S. Application Data

(63) Continuation of application No. 10/003,476, filed on Nov. 1, 2001, now Pat. No. 6,827,681.

(30) Foreign Application Priority Data

Jun. 28, 2001 (EP) .................................. 01114823

(51) Int. Cl.
*A61N 2/00* (2006.01)
(52) U.S. Cl. ......................................................... 600/9
(58) Field of Classification Search ............. 600/9–15, 600/26–28; 128/897–899
See application file for complete search history.

(56) References Cited

U.S. PATENT DOCUMENTS 3,967,616 A 7/1976 Ross
4,949,725 A 8/1990 Raviv et al.
5,119,816 A 6/1992 Gevins (Continued)

FOREIGN PATENT DOCUMENTS

GB 2 271 931 5/1994

(Continued)

OTHER PUBLICATIONS

Krings, T. et al. "Stereotactic Transcranial Magnetic Stimulation: Correlation with Direct Electrical Cortical Stimulation." *Neurosurgery*, vol. 41, No. 6, Dec. 1997, pp. 1319-1326.

(Continued)

*Primary Examiner*—John P. Lacyk
(74) *Attorney, Agent, or Firm*—Renner, Otto, Boisselle & Sklar, LLP

(57) ABSTRACT

The invention relates to a method for stimulating specific areas of a brain using an induction device, comprising the following steps: recording the spatial structure of the head, in particular the brain; generating a simulation model of the induction device; and arranging the induction device relative to the head such that a specific area of the brain determined by means of the simulation model of the induction device is stimulated by a current flowing in the induction device, as well as to a method for stimulating specific areas of a brain using an induction device, comprising the following steps: recording the spatial structure of the head, in particular the brain; generating a simulation model of the head; and arranging the induction device relative to the head such that a specific area of the brain determined by means of the simulation model of the head is stimulated by a current flowing in the induction device, as well as to a device for stimulating specific areas of a brain using an induction device connected to a marker.

13 Claims, 7 Drawing Sheets

U.S. PATENT DOCUMENTS

| | | | |
|---|---|---|---|
| 5,263,488 | A | 11/1993 | Van Veen et al. |
| 5,366,435 | A | 11/1994 | Jacobson |
| 5,441,495 | A | 8/1995 | Liboff et al. |
| 5,501,704 | A | 3/1996 | Chang et al. |
| 5,545,191 | A | 8/1996 | Mann et al. |
| 5,644,234 | A | 7/1997 | Rasche et al. |
| 5,687,724 | A | 11/1997 | Jewett et al. |
| 5,707,334 | A | 1/1998 | Young |
| 5,738,625 | A | 4/1998 | Gluck |
| 5,769,778 | A | 6/1998 | Abrams et al. |
| 5,833,600 | A | 11/1998 | Young |
| 6,014,582 | A | 1/2000 | He |
| 6,066,084 | A | 5/2000 | Edrich et al. |
| 6,129,685 | A | 10/2000 | Howard, III |
| 6,132,361 | A | 10/2000 | Epstein et al. |
| 6,234,953 | B1 | 5/2001 | Thomas et al. |
| 6,266,556 | B1 | 7/2001 | Ives et al. |
| 6,280,376 | B1 | 8/2001 | Holcomb |
| 6,351,659 | B1 | 2/2002 | Vilsmeier |
| 6,438,399 | B1 | 8/2002 | Kurth |
| 6,463,328 | B1 | 10/2002 | John |
| 6,491,620 | B1 | 12/2002 | Davey |
| 6,516,246 | B1 | 2/2003 | Derakhshan |
| 2003/0050527 | A1 * | 3/2003 | Fox et al. .................... 600/13 |

FOREIGN PATENT DOCUMENTS

WO      98/06342 A      2/1998

OTHER PUBLICATIONS

Ettinger, Gil J. et al. "Experimentation with a Transcranial Magnetic Stimulation System for Functional Brain Mapping." *Medical Image Analysis,* vol. 2, No. 2; Jun. 1998, pp. 133-142.

Ruohonen, J. et al. "Focusing and targeting of magnetic brain stimulation using multiple coils." *Medical & Biological Engineering & Computing,* (May 1998): pp. 297-301.

Ettinger, Gil J. et al. "Non-Invasive Functional Brain Mapping Using Registered Transcranial Magnetic Stimulation.", 1996 IEEE, Proceedings of MMBIA, p. 32-41, XP-002202005.

* cited by examiner

METHOD AND DEVICE FOR TRANSCRANIAL MAGNETIC STIMULATION

RELATED APPLICATION DATA

This application is a continuation of U.S. patent application Ser. No. 10/003,476 filed on Nov. 1, 2001 now U.S. Pat. No. 6,827,681, which is incorporated herein by reference in its entirety.

FIELD OF THE INVENTION

The present invention relates to a method and a device for transcranial stimulation, in particular for non-invasively localising specific areas of the brain, such as for example the so-called primary areas of the brain. In this way, for instance, brain functions may be mapped, i.e. assigned to specific areas of the brain.

BACKGROUND OF THE INVENTION

In various areas of medicine, such as for example neurology, psychiatry or brain surgery, it is desirable to be able to localise specific functional areas of the brain in order to be able to map brain functions. If, for example, a brain tumour is to be removed by surgery, then as far as possible the tumour should be removed without, however, possibly damaging the so-called primary areas of the brain which play a decisive role in a person's motor and sensory systems, language, or visual capabilities. Surgery should, if possible, not damage these areas at all, or only to an exceedingly small extent.

According to a known direct method, such specific areas of the brain have been found intra-operatively by direct cortical stimulation (DCS) on an exposed cranium using electrodes. In this process, an electrode was inserted into a specific area of the brain and an electrical impulse applied, wherein the reaction of the person being examined following the electrical impulse, for example the twitching of a muscle or the perception of visual impressions, is observed. The specific areas of the brain located by direct cortical stimulation were marked using small, attached plates which helped the surgeon's orientation in a subsequent brain operation with respect to areas of the brain which are as far a possible not to be damaged. To date, direct cortical stimulation still represents the most precise method for mapping brain functions, enabling accuracy in the range of a few millimeters when locating specific areas of the brain. However, this method can only be performed intra-operatively, the person under examination being fully conscious. This, however, can lead to problems in the application of this method, since this is an unpleasant state for the person being examined, and if complications arise, the person cannot simply be laid down and made to relax, due to the exposed cranium.

Furthermore, various indirect methods are known for mapping brain functions, by which, however, only a considerably lower accuracy in locating specific areas of the brain may be achieved. Thus, in functional nuclear spin tomography (fMRI) for example, a person under examination has to perform specific actions, such as for example a sweep of the hand, which promotes blood flow to the areas of the brain assigned to these actions. This change in the blood flow in specific areas of the brain may be measured during neuronal activity due to the decoupling of blood flow and oxygen consumption, since this gives rise to hyperoxygenation and thus a drop in the concentration of paramagnetic deoxyhaemoglobin (BOLD-effect), which may then be measured by means of suitable sequences of nuclear spin tomography as a so-called "endogenic contrast medium". However, as mentioned above, this method is relatively imprecise and only provides spatial resolution in the range 0.5 to 1.0 cm.

A method is known from *Neurosurgery* 1992–1998, December 1997, Volume 41, Number 6, 1319 *"Stereotactic Transcranial Magnetic Stimulation: Correlation with Direct Electrical Cortical Stimulation"*, wherein stereotactic transcranial magnetic stimulation (TMS) is used to pre-operatively functionally map the motor cortex. In this process, a patient's head is attached firmly and immovably to a headrest provided with a rotating arm, on which a figure-eight coil is arranged such that the tip of the arm lies beneath the intersecting point of the coil. In this way, the arm is aligned such that the tip lying beneath the intersecting point of the two coils points to a specific area in which a current is to be induced.

SUMMARY OF THE INVENTION

It is an object of the present invention to propose a method and a device for stimulating specific areas of a brain, by which application may be simplified and the spatial accuracy in stimulating and therefore in localising specific areas of the brain may be improved.

This object is solved by the subjects of the independent claims. Advantageous embodiments are given by the subclaims.

In accordance with a first aspect of the invention, the spatial structure of the brain is recorded, for example by means of a nuclear spin resonance method (MRI), computer tomography (CT) or another suitable method, in a method for stimulating specific areas of the brain, in order for instance to be able to non-invasively localise primary areas of the brain. In accordance with the invention, an induction device used for generating magnetic fields necessary for stimulation is examined before stimulation is begun. This calculates for example what kind of magnetic field is generated by the induction device at specific through-flowing currents, in particular where the magnetic field generated by the induction device is at its greatest, i.e. exhibits the greatest field strength, for example. In this respect, the wire-wound coil(s) of the induction device may for example be exactly examined optically, wherein the range or point of the maximum magnetic field which the induction device can generate may be calculated from these wire-wound coils. The induction device can also for example be x-rayed or examined by other suitable methods in order to carry out an exact analysis of the induction device's current carrying. As an alternative or a supplement to calculating the magnetic field which the induction device can generate, a measurement may also be taken to determine the spatial range or point of the greatest magnetic field which the induction device can generate, in relation to the induction device. In general, an induction device should, in accordance with the invention, be examined or analysed before being used for stimulating specific areas of the brain or for simulating the stimulation of specific areas of the brain, in order to determine the spatial positional relationship between the induction device and the range or point at which the maximum magnetic field is generated by the coil or at which the maximum electrical field induced by the magnetic field is generated. By using the result of this examination, a simulation model of the induction device may be produced, such that the induction device can be arranged relative to the brain to be examined in such a way that a desired area of the brain can be stimulated by a current flowing in the induction device. Thus, a strong magnetic field, as narrowly restricted as possible spatially, can be focussed on a small area of the brain.

In accordance with a further aspect of the present invention, a simulation model is produced of the head to be examined, wherein the data determined from recording the head's spatial structure may be used to improve the simulation model. The electrical or magnetic field generated by the induction device can thereby be relatively exactly focussed on a specific point in the brain by suitably positioning the induction device, since the layers over the brain which exhibit different conductivities act like various dielectrics which have a decisive influence on focusing the field on the brain.

The two methods described above for analysing and simulating the induction device and for modelling the head may be used separately or in combination, to further improve focussing the field generated by the induction device.

Using the method in accordance with the invention, transcranial magnetic stimulation (TMS) may be improved, and in particular made more precise, which enables specific areas of the brain, for example the aforementioned primary areas of the brain, to be precisely and non-invasively localised, which may for example improve pre-operative surgical planning. The methods in accordance with the invention may however also be used to examine or cure other brain dysfunctions, such as for example for diagnosing epilepsy or Parkinson's disease. By using the methods in accordance with the invention, it is possible to map brain functions exactly via an indirect method without having to open a person's cranium in order to directly access the brain.

The head is advantageously modelled by building a finite, multi-shelled model wherein electrical and/or magnetic fields for example may be calculated using finite-element methods and the individual shells advantageously modelled for example as nested spherical or ellipsoid shells with adjustable thicknesses, which may for instance be arranged concentrically. The model is particularly advantageously sub-divided into three shells, wherein the respective shells from the outermost in simulate the scalp, the cranial bones and the surface of the brain. These three different areas of the head exhibit different electrical and magnetic characteristics, such that modelling a head using three shells with for example different dielectric constants and/or different conductivities may for example provide very good results if the values used for the electrical and/or magnetic parameters come as close as possible to values determined or calculated in experiments. The shell model is also advantageously modified according to the recorded spatial structure of a head to be examined, wherein the shell model is adapted as exactly as possible to the geometry of a head to be examined, for example by extending and/or distorting or shifting individual shells.

Preferably, markers—particularly preferably, passive markers—are arranged on the head to be examined and/or on the induction device, in order to be able to track the induction device and/or the head. Referencing and tracking persons and/or instruments is known from the prior art and will not be described here in detail. The induction device and head are matched in order to thus be able to determine the relative position of the induction device and the head as precisely as possible. Using markers has the advantage that a person under examination does not have to be securely positioned, but rather specific areas of the brain can still be precisely stimulated, even for a person moving freely around a room.

An individual coil consisting of one or more windings, or a combination of coils, may for example be used as the induction device. It is particularly advantageous to use an induction device wherein two coils lying in a plane are adjacent to one another such that the coils approximately exhibit the shape of an "8".

An area of the brain is preferably stimulated by electrical impulses applied to the induction device which may have a build-up time in the range 1 $\mu$s to 1 ms and a duration of 10 to 1000 $\mu$s. In this way, the individual impulses can be applied with a periodic pattern.

The spatial structure of the surface of the brain determined by a recording is preferably displayed optically, advantageously together with a display of the simulated area of stimulation for the induction device's current position. With the aid of such an optical display, an operator can alter the position and size of the area of stimulation, for example by inclining the induction device sideways and/or by moving the induction device towards or away from the head, an as small as possible focus point being aimed for, in order to obtain as high a spatial resolution as possible when localising specific areas of the brain.

Advantageously, the induction device is automatically positioned relative to the head, the induction device being positioned, for instance by a movable robot arm having a number of degrees of freedom, in such a way that a multitude of points on the surface of the brain are stimulated, with a focus point which is as small as possible. In this respect, the robot arm may be firmly attached to the head. In this way, suitable points of stimulation on the surface of the brain may for example be selected by pattern-recognition software and/or pre-set by an operator, which the robot arm then automatically moves to, such that the positioned induction device stimulates as small an area of the surface of the brain as possible. For automatic positioning, the simulation model of the induction device and/or of the head may be used.

In accordance with a further aspect of the invention, a device is proposed for stimulating specific areas of a brain, wherein an induction device is provided which is firmly connected to markers, preferably passive markers. Such an induction device provided with markers can be simply and precisely positioned in accordance with the invention, in order to stimulate a specific area of the brain with as small a focus point as possible.

Markers are also advantageously arranged on the head to be examined, in a fixed spatial arrangement, which may be detected by a position detection device similarly to the markers connected to the induction device. Preferably, a simulation device is also provided, with which the area to be stimulated in the brain may be determined by the induction device, wherein a model of the induction device and/or of the head as described above may be used to simulate the area of stimulation.

Advantageously, a display device is provided to display the relative position of the induction device and the brain, or to display the stimulation field on the brain which can be generated by the induction device, allowing an operator to position the induction device as precisely as possible relative to the brain, before a stimulation impulse is released.

The device in accordance with the invention advantageously comprises a device for automatically positioning the induction device relative to the brain, such as for example a robot arm which is movable to a number of degrees of freedom, i.e. which for example comprises one or more joints, such that the induction device may for example be moved towards or away from the head, or inclined with respect to the surface of the head, in order to make an area of stimulation on the brain which can be generated by the induction device as small as possible.

BRIEF DESCRIPTION OF THE DRAWINGS

The invention will now be described by way of preferred example embodiments. The drawings show.

DETAILED DESCRIPTION OF THE INVENTION

Figure 1:
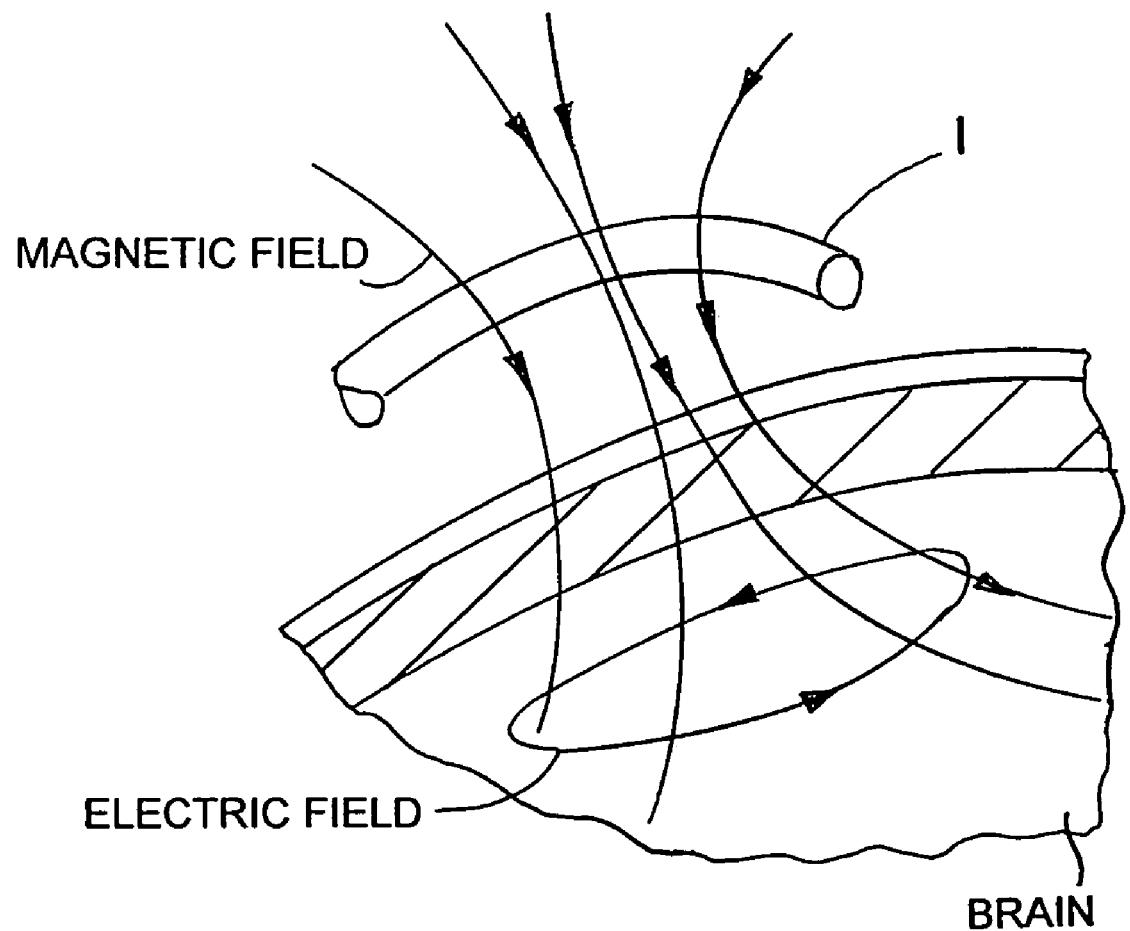
FIG. 1 a schematic representation of a three-shell model used in accordance with the invention.

FIG. 1 shows in diagram form a three-shell model of a head in accordance with the invention, wherein: the outer shell I models the scalp; beneath the scalp modelled by the outer shell I lies the second shell II which models the cranial bones. The inner area of the three-shell model is formed by the brain or surface of the brain III. A current in the induction device 1, shown schematically as a coil, creates the schematically shown magnetic field which comes out of the induction device and passes through the scalp and through the cranial bones, in order to induce an electrical field in the brain (these respectively modelled by the three shells I, II and III), which causes a ring-shaped flow of current by which a specific area of the brain is stimulated. Modelling the scalp, cranial bones and brain using two outer shells I and II surrounding the modelled brain III enables the induction device 1 to be positioned at a specific point, at a specific distance from the brain and at a specific angle of inclination relative to the surface of the brain, in order to concentrate the electrical field induced on the surface of the brain by the magnetic field of the induction device into as small an area as possible, to thus obtain as strong a focus as possible.

Figure 2A:
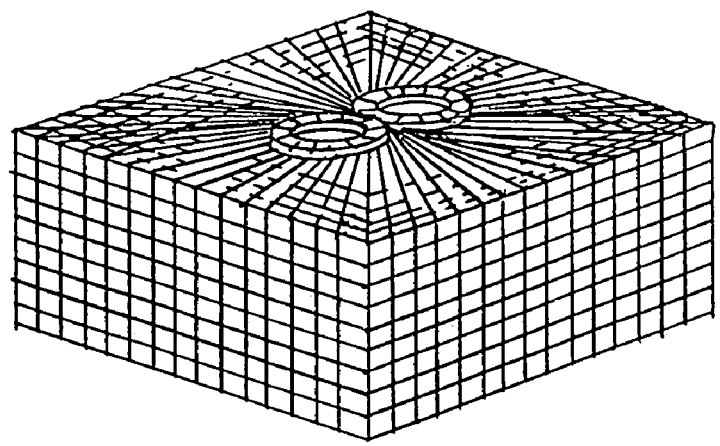
FIG. 2a a schematic representation of a simulation model according to the prior art.

FIG. 2a shows in diagram form a model which has been used hitherto for modelling an electrical field generated by two adjacent coils lying in a plane and forming the induction device 1. This, however, has not taken into account the fact that, due to the curvature of the head, the electrical field induced on the surface of the brain by the induction device 1 is affected by curved shells with different conductivities and dielectric constants.

Figure 2B:
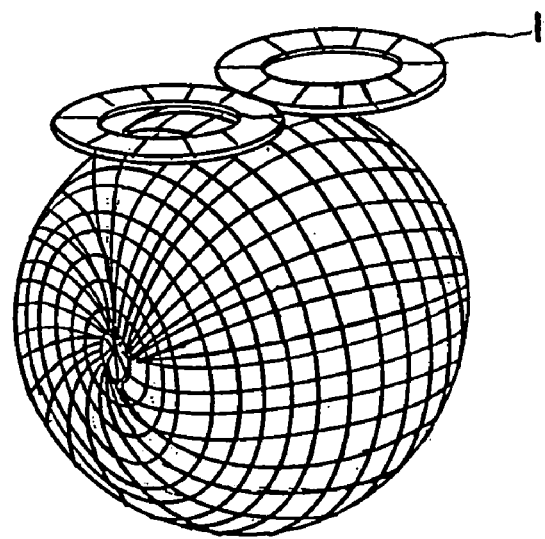
FIG. 2b a schematic representation of the simulation model in accordance with the invention.

FIG. 2b shows in diagram form the outer shell I of the three-shell model in accordance with the invention, with the induction device 1 lying over it, enabling a head to be more exactly modelled and thereby an induced electrical, field to be more exactly focussed.

Figure 3:
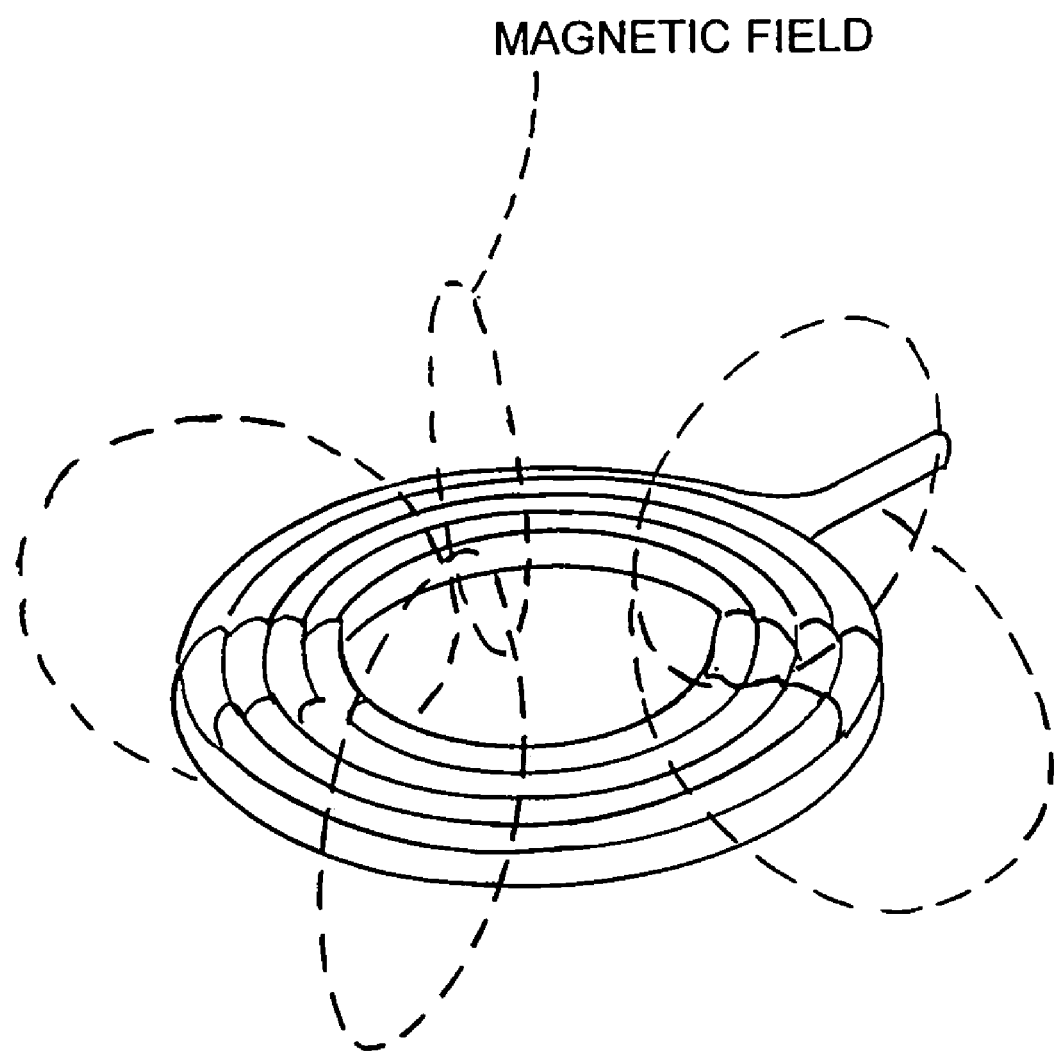
FIG. 3 a schematic representation of a coil which may be used as the induction device.
Figure 4A:
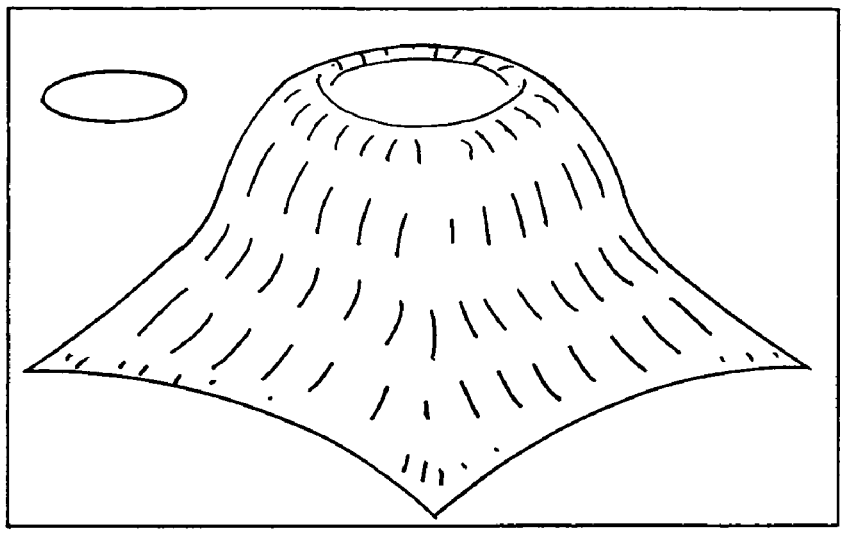
FIG. 4a the magnetic field generated by an individual coil.
Figure 4B:
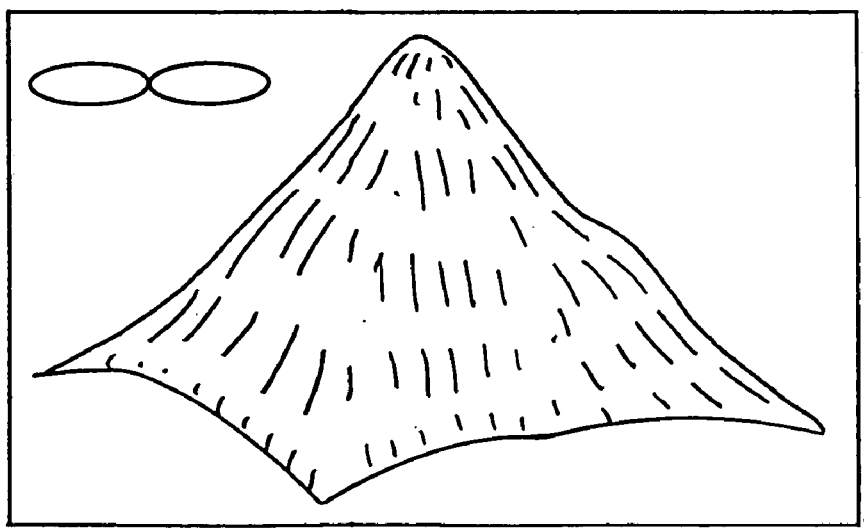
FIG. 4b the magnetic field generated by two adjacent coils.

FIG. 3 shows in diagram form a coil comprising a number of windings which may for example be used as a partial element of the induction device 1 shown in FIG. 2b. As may be seen from FIG. 3, the coil is not formed from concentrically nesting conductors, but from a single conducting element developed in the shape of a spiral, which leads to a slight asymmetry of the magnetic field generated by such a spiral-shaped conducting element. The concretely used induction device must thus be examined in order to obtain a good simulation model. The assumption, for example, that the maximum in a magnetic field generated from a figure-eight coil is beneath the intersecting point is not generally the case due to the asymmetry of a wire-wound coil, and leads to poor results in TMS. A magnetic field generated by, for example, two adjacent coils wound in the shape of a spiral exhibits the field strength distribution shown in diagram form in FIG. 4b. By comparison, FIG. 4a shows the field generated by just one coil. It can easily be seen that with a high field strength, better focus can advantageously be realised by a double coil arrangement. Due to the ring-shaped maximum, the magnetic field strength distribution shown in FIG. 4a, generated by a single coil, cannot be focussed onto a small area as well as the magnetic field in FIG. 4b, generated by a double coil, which has a clear, pointed maximum.

Figure 5:
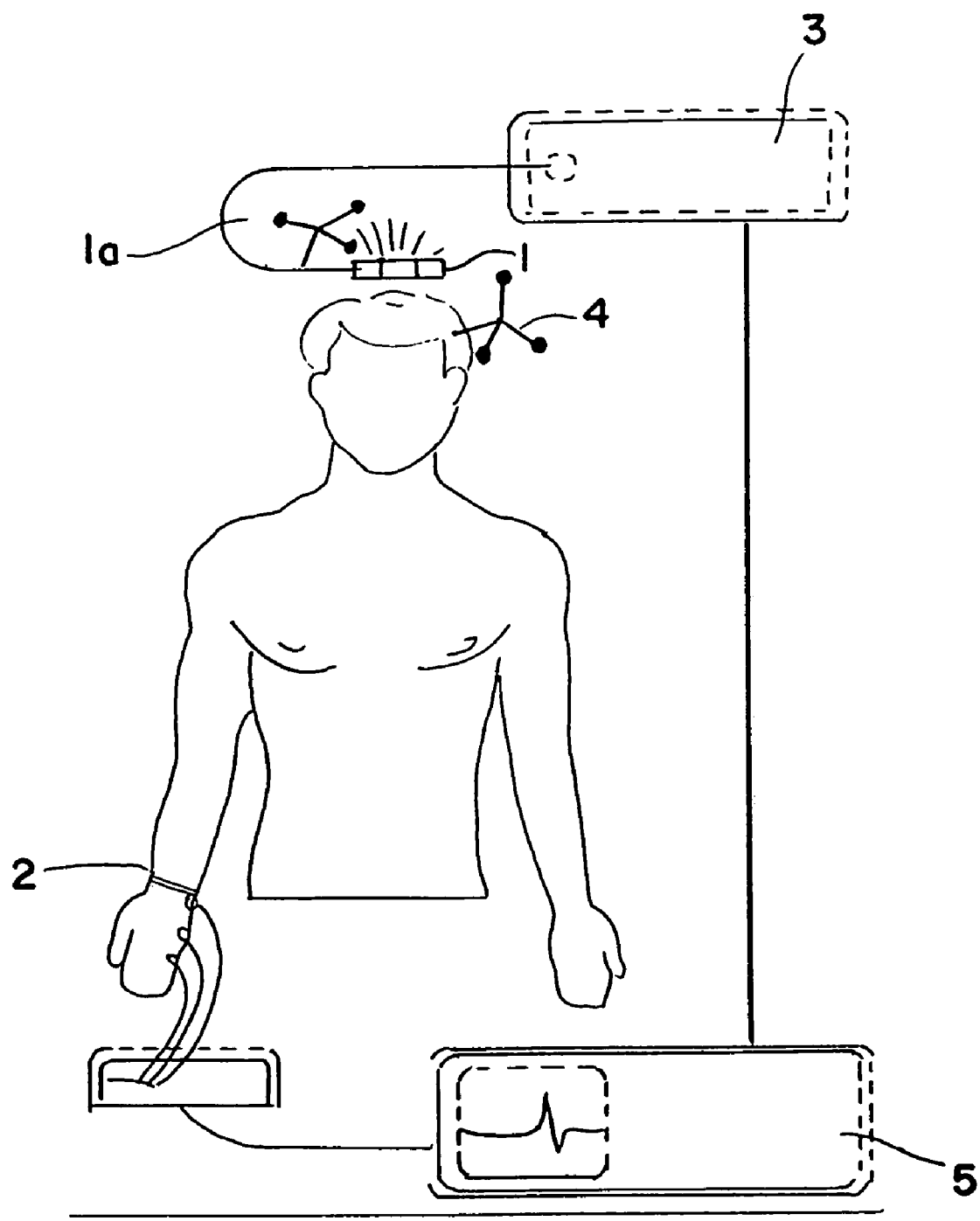
FIG. 5 a schematic diagram of the device in accordance with the invention, for stimulating specific areas of the brain.

FIG. 5 shows in diagram form a device in accordance with the invention for stimulating specific areas of a brain, wherein an induction device 1 connected to a reference star 1a is connected to a guiding device 3 which generates impulses, to stimulate specific areas in the brain of the person shown, on whom a further reference star 4 is arranged securely. If, for example, a motor area of the brain is stimulated, then a stimulus impulse can be measured by an electromyography (EMG) measurement, as shown for example on the measuring device 5, by means of a surface electrode 2 arranged for example on the person's arm. By back-coupling the measuring device 5 to the guiding device 4, the motor area can automatically be localised as exactly as possible, the induction device 1 for example being automatically placed in a suitable position for one or more stimulations by means of a robot arm.

Figure 6:
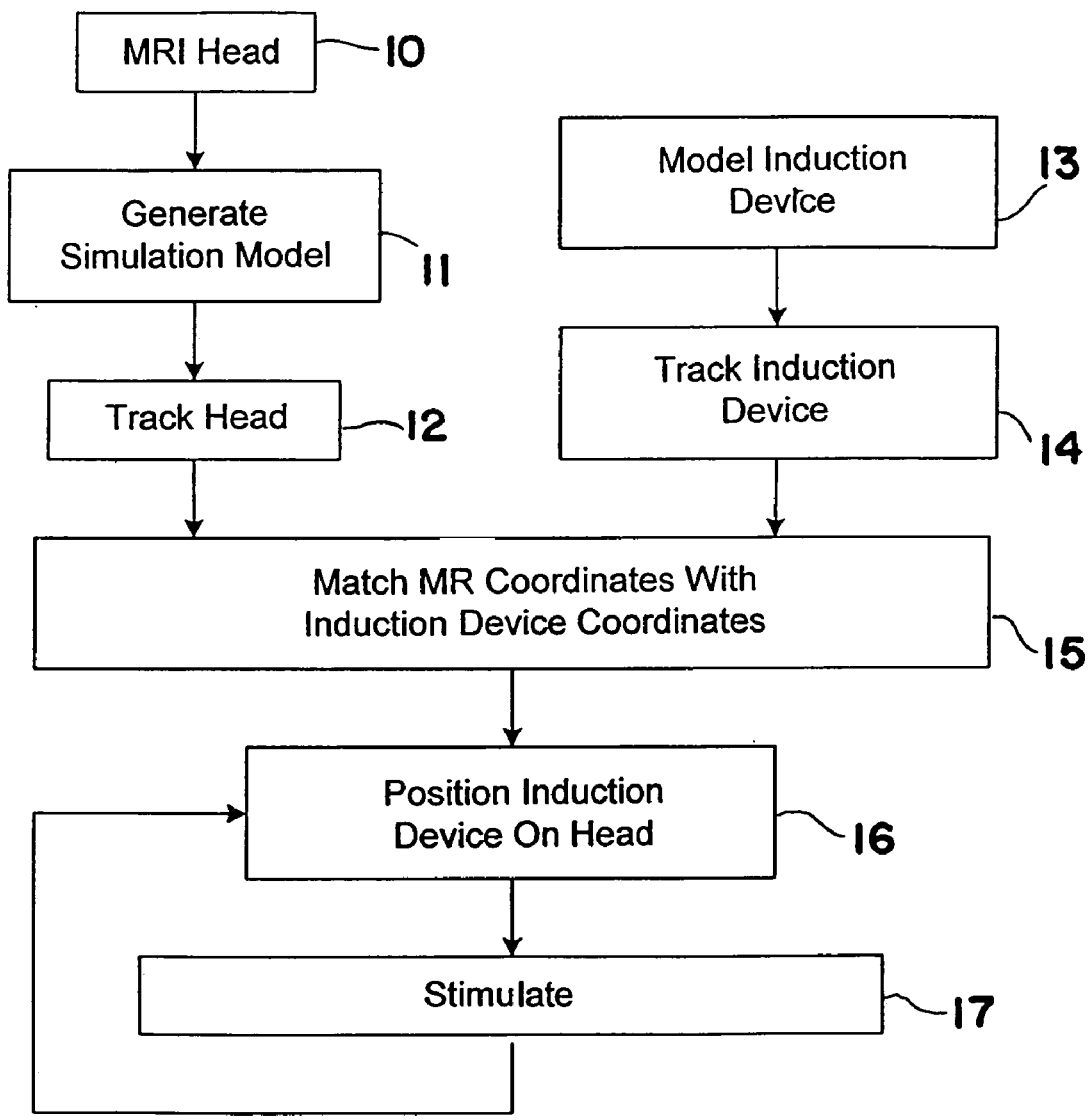
FIG. 6 a flow chart of an embodiment of the method in accordance with the invention.

FIG. 6 shows in diagram form the flow chart for an embodiment of the method in accordance with the invention. In a first step 10, the spatial structure of a head together with the brain is recorded using nuclear spin resonance (MRI). The data obtained in step 10 are used in step 11 to generate a simulation model of the recorded head, wherein for example as described above, the scalp, cranial bones and brain are modelled as three areas I, II and III, each exhibiting a characteristic dielectric constant and a characteristic conductance. The head is connected to a reference star 4, as shown in FIG. 5, through which its spatial position may be simply detected at any time (tracking).

In step 13, the induction device 1 used is modelled, wherein data which obtained from an exact examination of the spatial structure of conductors and/or coils contained in the induction device may be used to model it, such that a magnetic field which can be generated by the induction device may be relatively exactly calculated and simulated. Furthermore, the induction device can also b modelled by evaluating measurements from the magnetic field generated by the induction device. By modelling, a focus range of a concretely used induction device may be relatively exactly determined. As shown in FIG. 5, the induction device is connected to a reference star 1a, by which the induction device may be tracked, similarly to the head connected to a reference star 4.

In step 15, the co-ordinates of the head and thus of the spatial position of the structure of the brain obtained by MRI are aligned (matched) with the co-ordinates of the induction device, from which the spatial position of the induction device relative to the spatial structure of the head, in particular of the brain, determined by nuclear spin tomography may be obtained. By using this now known spatial positional relationship, the induction device can be positioned on the head in step 16, wherein the modelling data of the induction device and the modelling data of the head are used to simulate the induction range generated on the brain by the current flow of the induction device. If positioning is such that as small an area of the brain as possible is stimulated by the induction device in the simulation, then this area already determined by a simulation is stimulated in step 17. An observer can then establish what specific reactions a person shows when this specific area is stimulated, wherein it can be determined by way of these reactions, such as for example the twitching of a muscle, disruption to speech or the like, whether the stimulated area of the brain possesses a specific function. If this process of positioning and stimulating is carried out for a multitude f areas of the brain by repeating steps 16 and 17, then brain functions may be mapped, wherein in particular the primary areas of the brain of the person under examination may be localised. In this way, the induced electrical field desired must be calculated anew using the simulation models, wherein for example up to seven degrees of freedom (three for translation, three for rotation, and one for coil current) must be taken into account with respect to the induction device.

Figure 7:
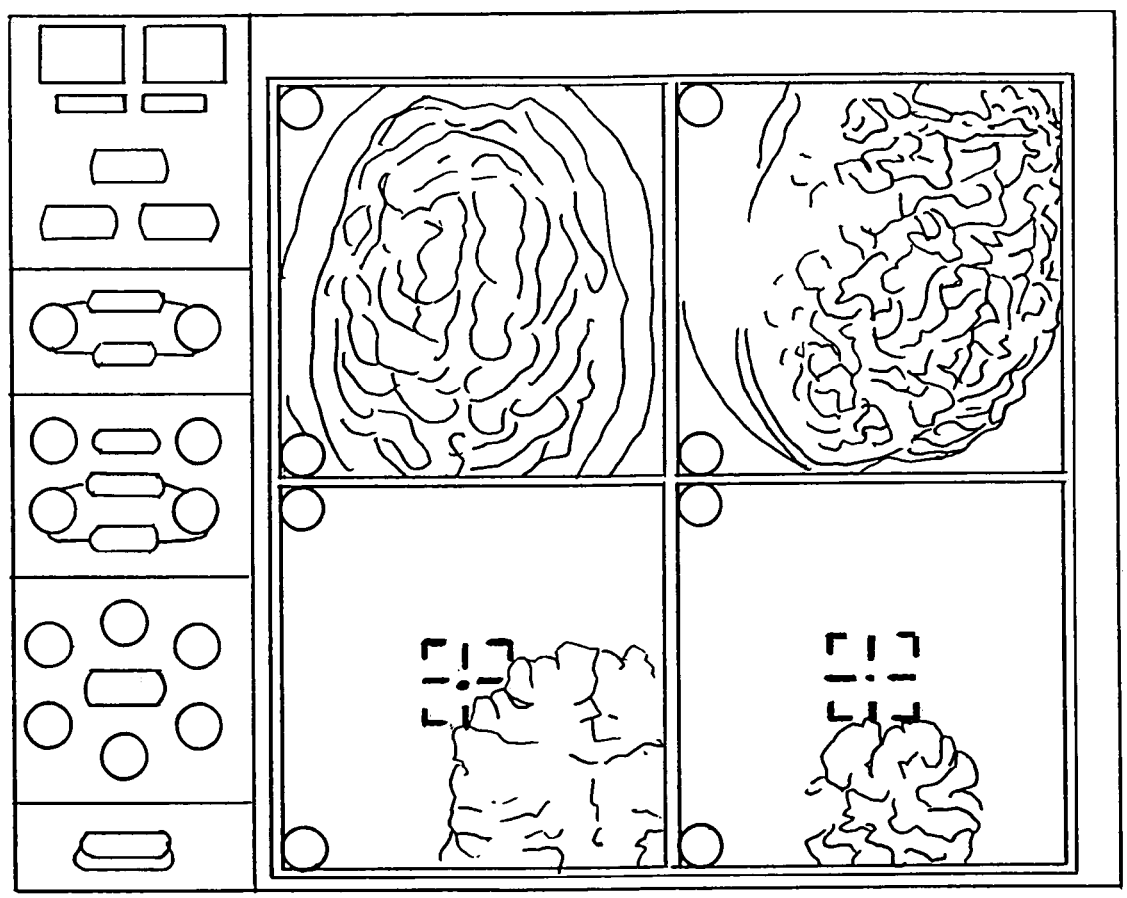
FIG. 7 a screen display of the brain with a simulated area of stimulation to assist in exactly positioning the induction device.

FIG. 7 shows in the two upper halves of the image the structure of a brain based on data obtained through nuclear spin resonance from two different angles of view. The two images beneath show the position of the induction device relative to the brain, wherein the induction device may be placed according to displayed guidance signals in a suitable position for stimulation.

What is claimed is:

1. A device for non-invasively stimulating specific areas of a brain within a head, said device comprising:
   a non-invasive induction device;
   at least one marker connected to the non-invasive induction device, said at least one marker being detectable by a tracking system.

2. The device as set forth in claim 1, wherein the induction device is a coil in the form of an eight.

3. A system for stimulating specific areas of the brain using an induction device having at least one tracking system detectable marker attached to the induction device, said system comprising:
   at least one marker connected to the head;
   a position detection device which detects the position of the at least one marker connected to the induction device and the at least one marker connected to the head; and
   a simulation device which determines the area of stimulation in the brain to be stimulated by the induction device, wherein a model of the induction device and/or of the head is used for simulating.

4. The system as set forth in claim 3, said system comprising:
   a display device which displays areas on the brain to be stimulated by the induction device.

5. The system as set forth in claim 3, said system comprising:
   a device for automatically positioning the induction device.

6. The system as set forth in claim 5, wherein the device for automatically positioning the induction device is a rotating robot arm.

7. The system as set forth in claim 3, wherein the at least one marker connected to the head is a passive marker.

8. The system as set forth in claim 3, said system further comprising:
   a device which generates a simulation model of the induction device.

9. The system as set forth in claim 8, said system further comprising:
   a device which generates a simulation model of the head.

10. The system as set forth in claim 9, wherein the device which generates a simulation model of the head uses a finite, multi-shelled model.

11. The system as set forth in claim 10, wherein the device which generates a simulation model of the head uses a model including a plurality of nested spherical or ellipsoidal shells having adjustable thicknesses.

12. The system as set forth in claim 11, wherein the device that generates a simulation model of the head assigns different dielectric constants to each of the plurality of nested spherical or ellipsoidal shells.

13. The system as set forth in claim 3, said system further comprising:
   a device that provides electrical impulses to the induction device.

* * * * *